(12) United States Patent
Lee

(10) Patent No.: US 7,604,659 B2
(45) Date of Patent: Oct. 20, 2009

(54) METHOD AND APPARATUS FOR REPAIR OF TORN ROTATOR CUFF TENDONS

(76) Inventor: James M. Lee, 514 Joyce St., Orange, NJ (US) 07050

( * ) Notice: Subject to any disclaimer, the term of this patent is extended or adjusted under 35 U.S.C. 154(b) by 801 days.

(21) Appl. No.: 10/983,742

(22) Filed: Nov. 9, 2004

(65) Prior Publication Data

US 2006/0100629 A1 May 11, 2006

(51) Int. Cl.
*A61B 17/86* (2006.01)
*A61F 2/08* (2006.01)

(52) U.S. Cl. ..................................... 606/319

(58) Field of Classification Search ......... 606/300–304, 606/309–312, 314, 317–319; 623/11.11, 623/13.11–13.14; 411/531, 540
See application file for complete search history.

(56) References Cited

U.S. PATENT DOCUMENTS

| | | | | |
|---|---|---|---|---|
| 2,092,682 A | * | 9/1937 | Roske | ......................... 411/531 |
| 3,431,813 A | * | 3/1969 | Johnson | ......................... 411/61 |
| 4,988,351 A | | 1/1991 | Paulos et al. | |
| 5,013,316 A | | 5/1991 | Goble et al. | |
| 5,702,398 A | | 12/1997 | Tarabishy | |
| 5,720,753 A | | 2/1998 | Sander et al. | |
| 5,840,078 A | | 11/1998 | Yerys | |
| 6,056,751 A | | 5/2000 | Fenton, Jr. | |
| 6,162,234 A | | 12/2000 | Freedland et al. | |
| 6,746,191 B2 | * | 6/2004 | Edland | ......................... 411/34 |
| 2003/0105465 A1 | | 6/2003 | Schmieding et al. | |

* cited by examiner

*Primary Examiner*—Anu Ramana
(74) *Attorney, Agent, or Firm*—Jacobson Holman PLLC

(57) ABSTRACT

A minimally invasive orthopedic fastener for the repair of torn rotator cuff tendons. The rotator cuff is thereby repaired transarthroscopically to bring the tendons tight to the bone. This is accomplished by the use of a bone screw having a plurality of vanes pivotally mounted thereon. The vanes are pivotal from a retracted position extending along a length of the screw to an extended position extending substantially perpendicular to the shaft of the screw. The fastener is cannulated and taken down over a guide wire through a minimal incision to the operative site. Under direct vision, the screw is initially rotated into the bone by a screwdriver passed from the proximal end of the cannula to the distal end of the cannula to engage the fastener. The cannula is then partially withdrawn and by continued rotation of the screw, the vanes are moved into a position substantially perpendicular to the screw, thereby entrapping the tendons between the vanes of the screw and the bone.

11 Claims, 6 Drawing Sheets

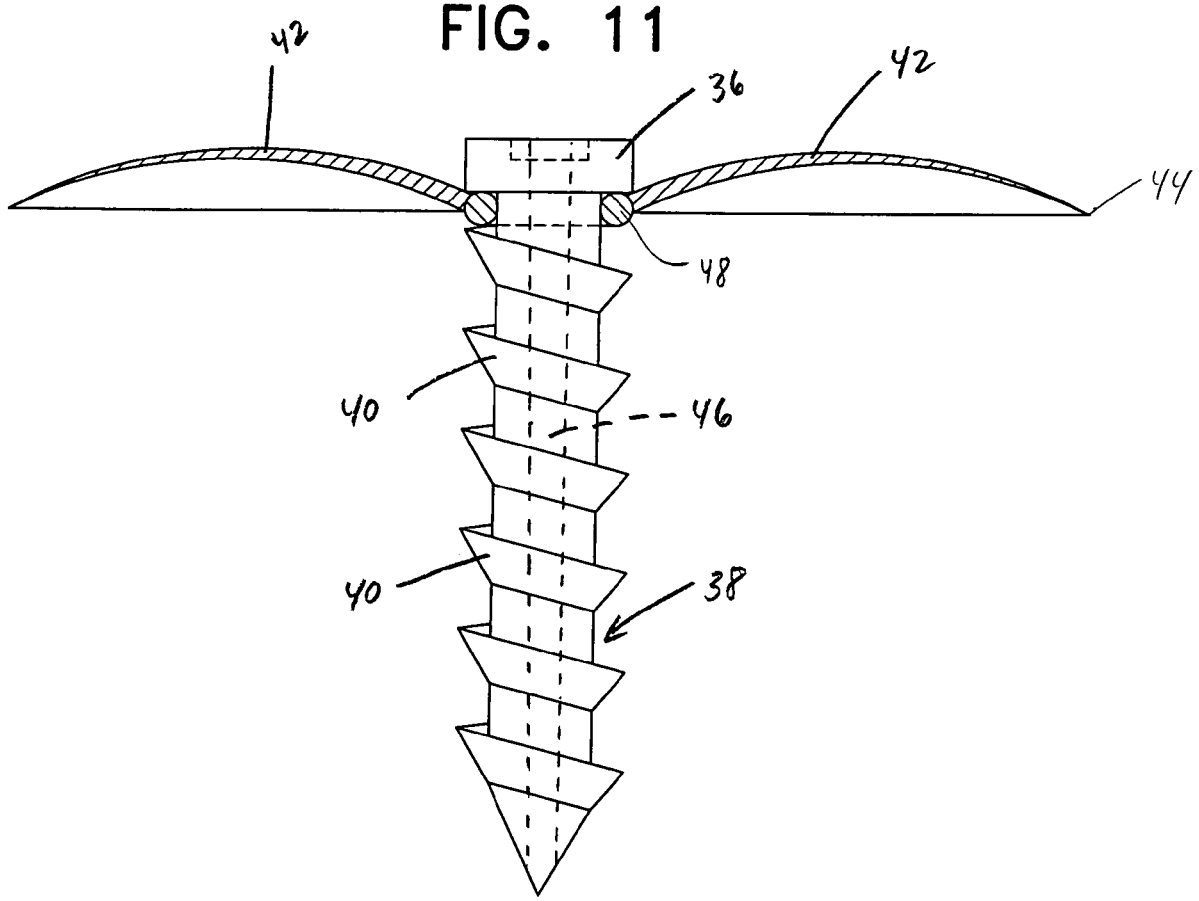

METHOD AND APPARATUS FOR REPAIR OF TORN ROTATOR CUFF TENDONS

FIELD OF THE INVENTION

The present invention relates to a method and apparatus for repair of torn rotator cuff tendons. A cannula and an orthopedic fastener are passed over a guide wire to the site of the tear through a minimal incision. The fastener includes a plurality of pivotally mounted vanes which are compressible in the cannula and extendable at the repair site for securing a torn tendon to the bone.

BACKGROUND OF THE INVENTION

At the meeting of the clavicle, scapula, humerus and overlying soft parts, the shoulder is subject to great stress and forces. Over exertion of the shoulder sometimes can lead to a tearing of the rotator cuff tendons.

Various systems have been proposed for orthopedically repairing soft tissue. Examples of such systems are found in U.S. Pat. Nos. 5,840,078, 5,702,398, 4,988,351, 6,162,234, 6,056,751, 5,720,753, 5,013,316 and U.S. Publication No. 2003/0105465.

These various systems usually require unnecessarily large invasive techniques for repair of tendons.

SUMMARY OF THE INVENTION

Accordingly, it is an object of the present invention to provide a minimally invasive orthopedic fastener for the repair of torn rotator cuff tendons. The rotator cuff is thereby repaired transarthroscopically to bring the tendon tight to the bone.

This is accomplished by the use of a bone screw having a plurality of vanes pivotally mounted thereon. The vanes are pivotal from a retracted position extending along a length of the screw to an extended position extending substantially perpendicular to the shaft of the screw.

The fastener is cannulated and taken down over a guide wire through a minimal incision to the operative site. Under direct vision, the screw is initially rotated into the bone by a screwdriver passed from the proximal end of the cannula to the distal end of the cannula to engage the fastener.

The cannula is then partially withdrawn and by continued rotation of the screw, the vanes are moved into a position substantially perpendicular to the screw, thereby entrapping the tendons between the vanes of the screw and the bone. The cannula and screw driver are then withdrawn. Several bone screws are placed into position transarthroscopically using only a minimal incision for repair of a torn rotator cuff.

It is therefore another object of the present invention to provide an orthopedic fastener for securing tendons to the bone for repair of torn rotator cuff tendons.

It is another object of the present invention to provide an orthopedic fastener for securing tendons to the bone for repair of torn rotator cuff tendons using a bone screw having a plurality of pivotally mounted vanes which lie adjacent a shaft of the screw during passage through a cannula and expand to a position substantially perpendicular to the shaft of the screw for retaining tendons against the bone into which the screw is inserted.

It is still yet another object of the present invention to provide an orthopedic fastener for securing tendons to the bone for repair of torn rotator cuff tendons using a bone screw having a plurality of pivotally mounted vanes which lie adjacent a shaft of the screw during passage through a cannula and expand to a position substantially perpendicular to the shaft of the screw for retaining tendons against the bone into which the screw is inserted with the vanes being curved symmetrically along their length to form a clover leaf appearance when securing the tendons to the bone.

These and other objects of the invention, as well as many of the intended advantages thereof, will become more readily apparent when reference is made to the following description taken in conjunction with the accompanying drawings.

BRIEF DESCRIPTION OF THE DRAWINGS

FIG. 11 is an enlarged, partial sectional view of the fastener shown in FIG. 9 to illustrate the pivotally mounted vanes secured to an O-ring surrounding an upper end of the shaft of the screw, just below the head of the screw.

DETAILED DESCRIPTION OF THE PREFERRED EMBODIMENTS

Figure 1:
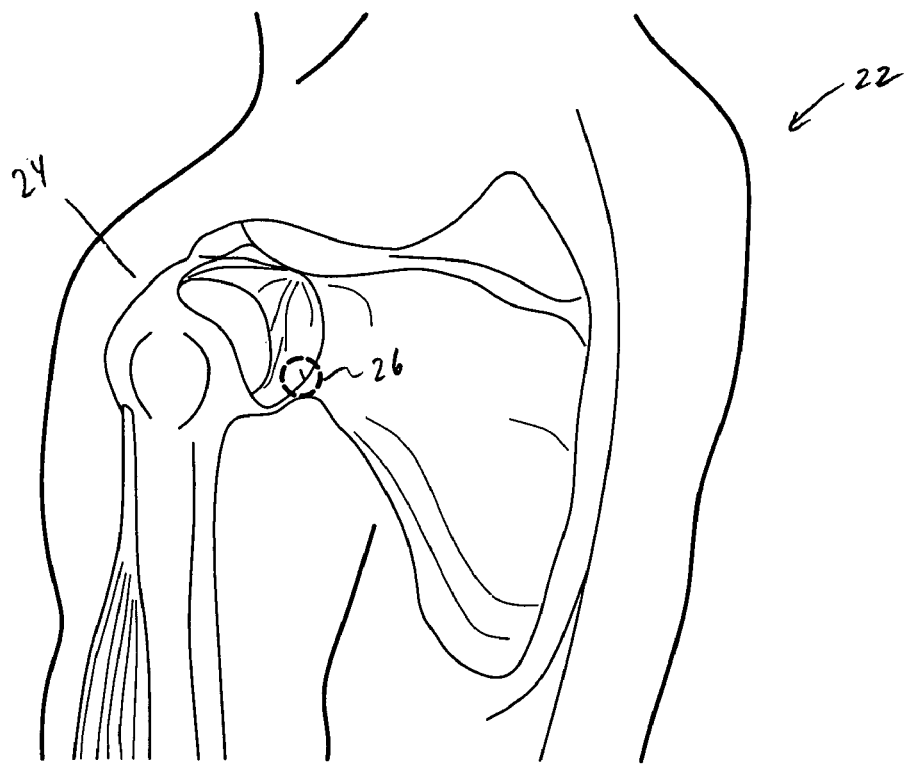
FIG. 1 is a schematic view of an arthroscopic examination of the shoulder with an area encircled which will form the site for implantation of the orthoscopic fastener of the present invention.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

With reference to the drawings, and to FIGS. 1 through 5, in particular, an orthopedic fastener embodying the teachings of the subject invention is generally designated as 20. With reference to FIG. 1, a person 22 is shown with a skeletal and tendon illustration of the shoulder 24, with particular emphasis directed toward encircled area 26. An enlargement of area 26 is shown in FIGS. 2 through 5 with respect to locating an orthopedic fastener in this region of the shoulder 24 so as to repair torn rotator cuff tendons.

Figure 2:
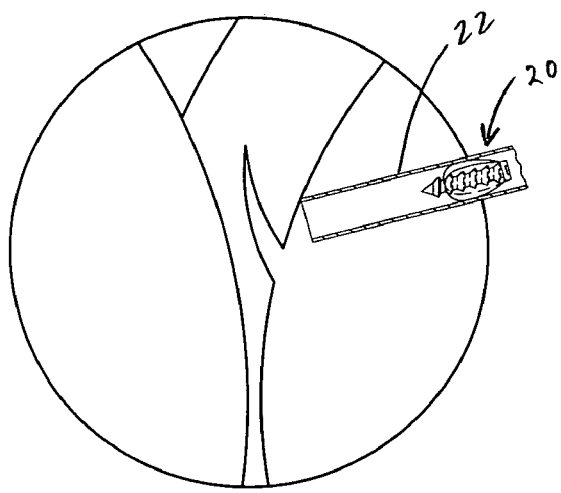
FIG. 2 is a schematic view illustrating the approach of a cannula to a torn tendon site with a collapsed orthoscopic fastener of the present invention located inside the cannula.
Figure 3:
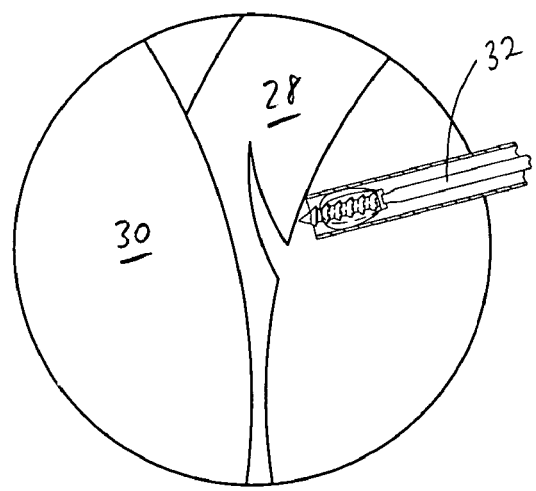
FIG. 3 is a schematic view illustrating initial rotation of the orthoscopic fastener of the present invention by a driver passing through the cannula to compress the torn tendon against the bone.

As shown in FIG. 2, the orthopedic fastener 20 is located in a cannula 22. The cannula is positioned through a minimal incision in the shoulder and passed to the area of the shoulder in need of repair. The fastener 20 is hollow to facilitate the insertion of the fastener and cannula 22 over a guide wire to the position shown in FIG. 2.

After locating the fastener proximate to the torn tendon 28, and adjacent to bone 30, the guide wire is retracted and the fastener driver 32 is inserted through the cannula to engage with a complementary shaped recess 34 in the head 36 of the fastener 20.

Figure 4:
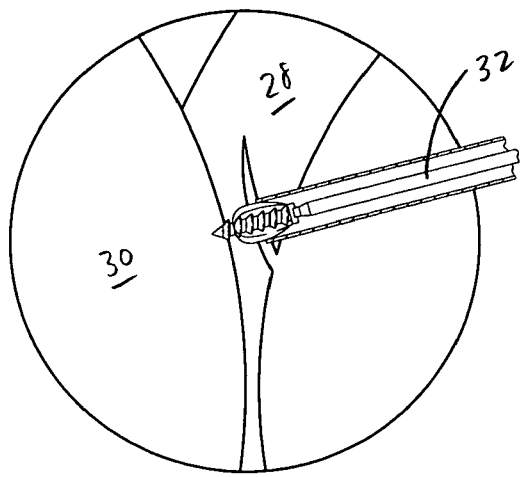
FIG. 4 schematically illustrates the initial insertion of the screw portion of the orthoscopic fastener into the bone while compressing the torn tendon towards the bone.

As shown in FIG. 4, by rotation of the driver, the fastener 20 is moved out of the distal end of the cannula to penetrate the tendon 28 and bone 30. Continued rotation of the fastener causes a shaft portion 38 having spiral flutes 40 to pass into the bone 30.

Simultaneous with the retraction of the cannula 22, a plurality of pivotally mounted vanes 42 having a tip portion 44 engage and then spread across tendon 28. Upon continued rotation of the fastener, the vanes 42 first trap and then compress the tendon 28 against the bone 30.

Figure 5:
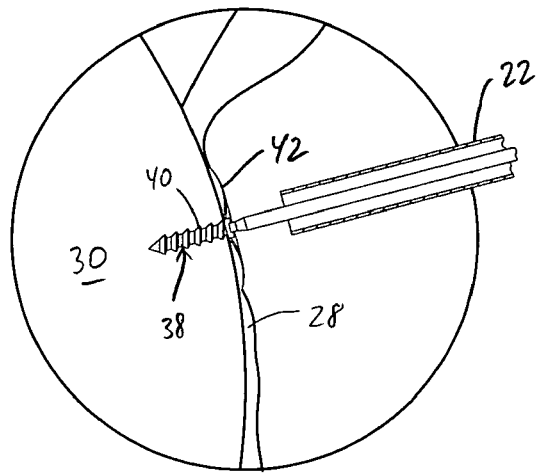
FIG. 5 schematically illustrates the rotation of the screw portion into the bone while withdrawing the cannula to expose the plurality of vanes pivotally mounted on the shaft of the screw so as to engage the tendons and by continued rotation of the screw into the bone, causing the vanes to compress the tendons onto the bone.
Figure 6:
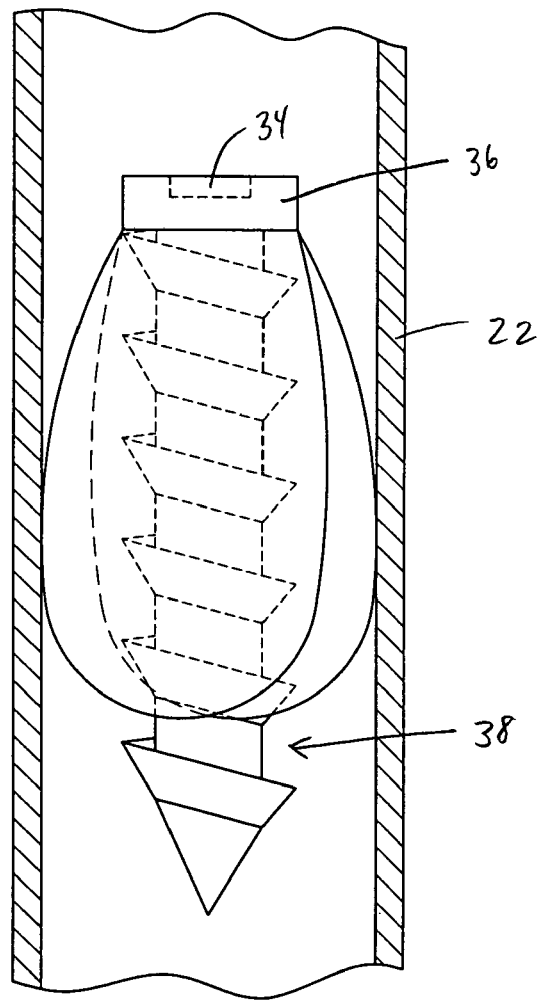
FIG. 6 is an enlarged detailed view of the orthoscopic fastener of the present invention in a retracted position having its vanes folded along a side of the shaft of the screw.
Figure 7:
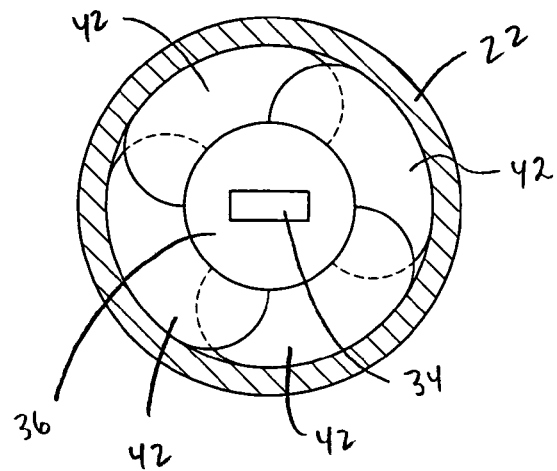
FIG. 7 is a top sectional view illustrating the orthoscopic fastener in a compressed condition within the cannula.
Figure 8:
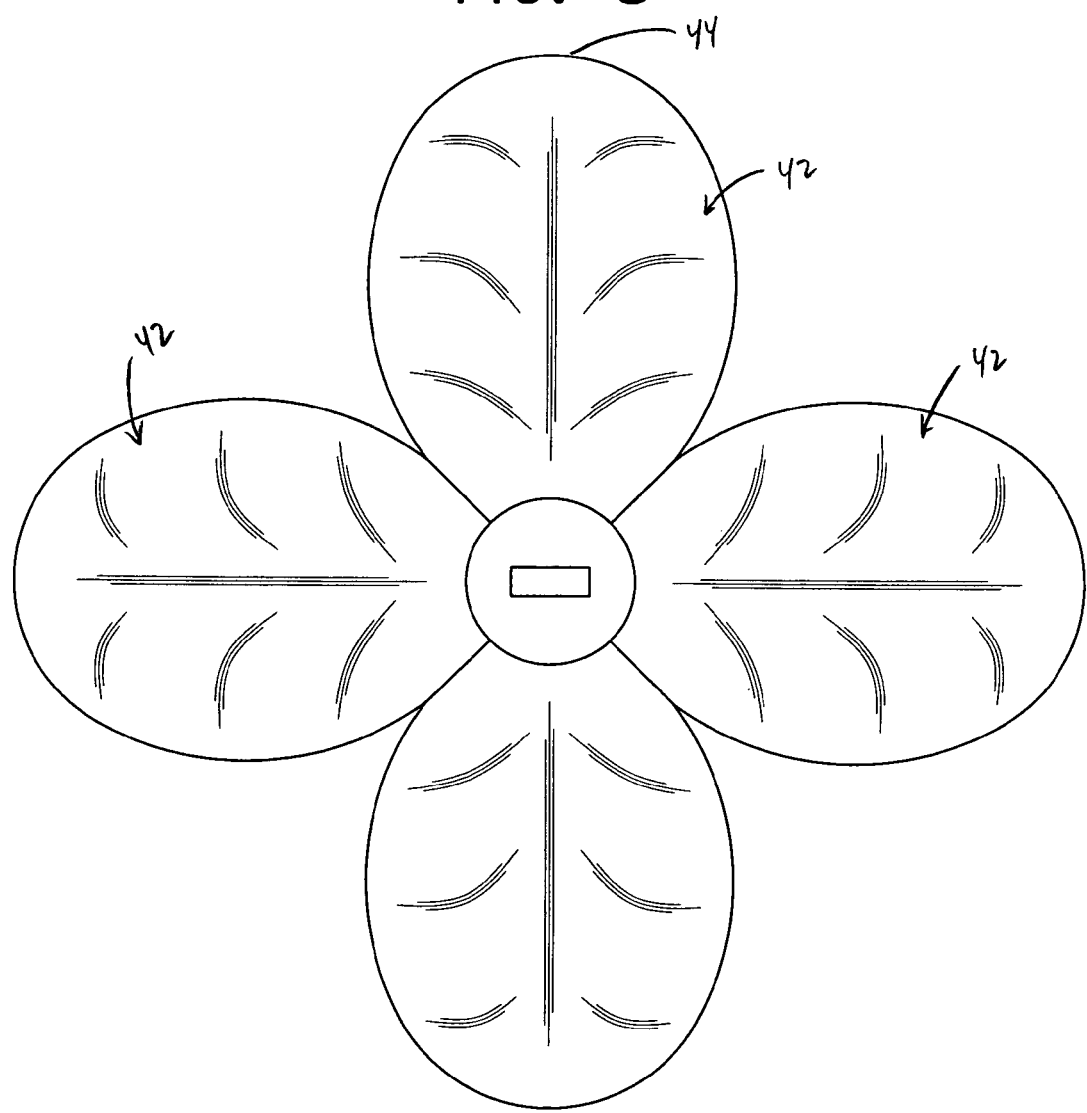
FIG. 8 is an enlarged view of the vanes of the orthoscopic fastener of the present invention in an expanded position.
Figure 9:
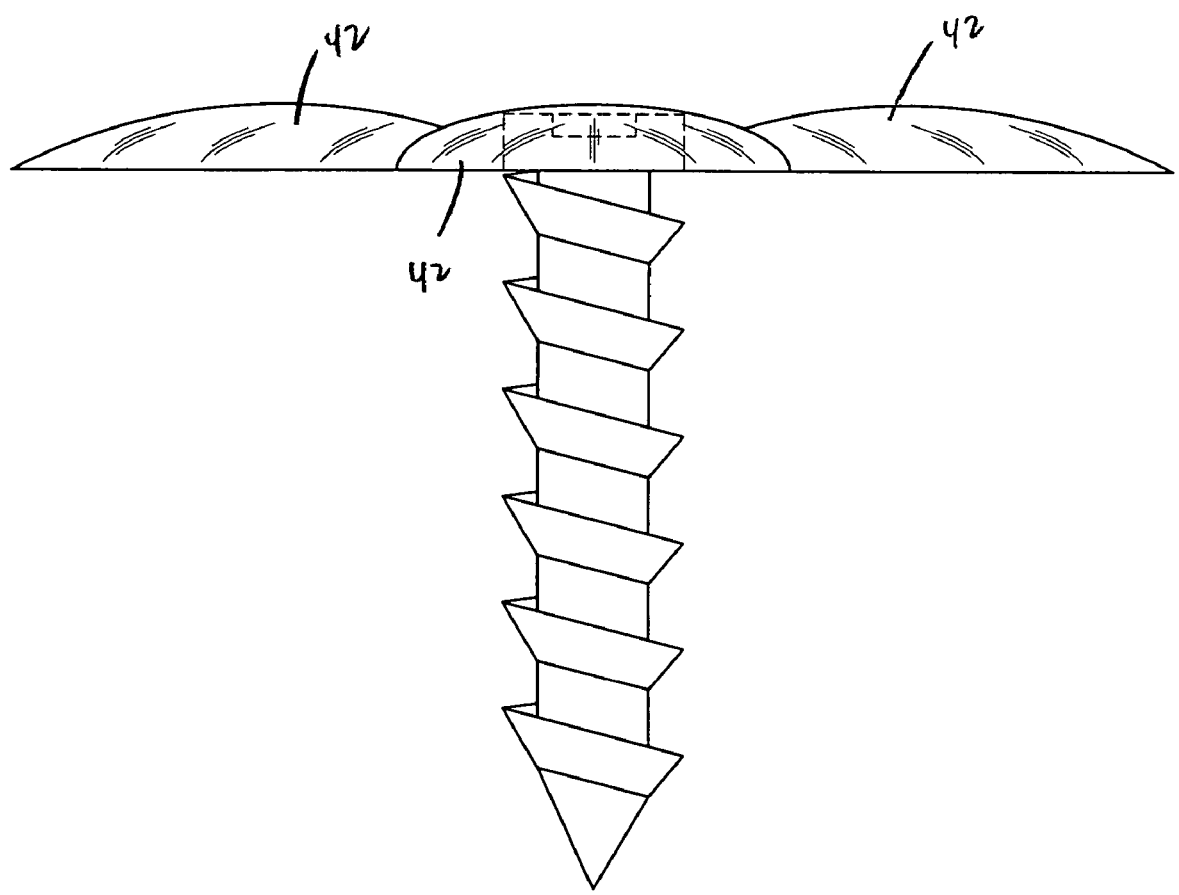
FIG. 9 is an enlarged side view of the orthoscopic fastener of the present invention with the vanes in an extended position.
Figure 10:
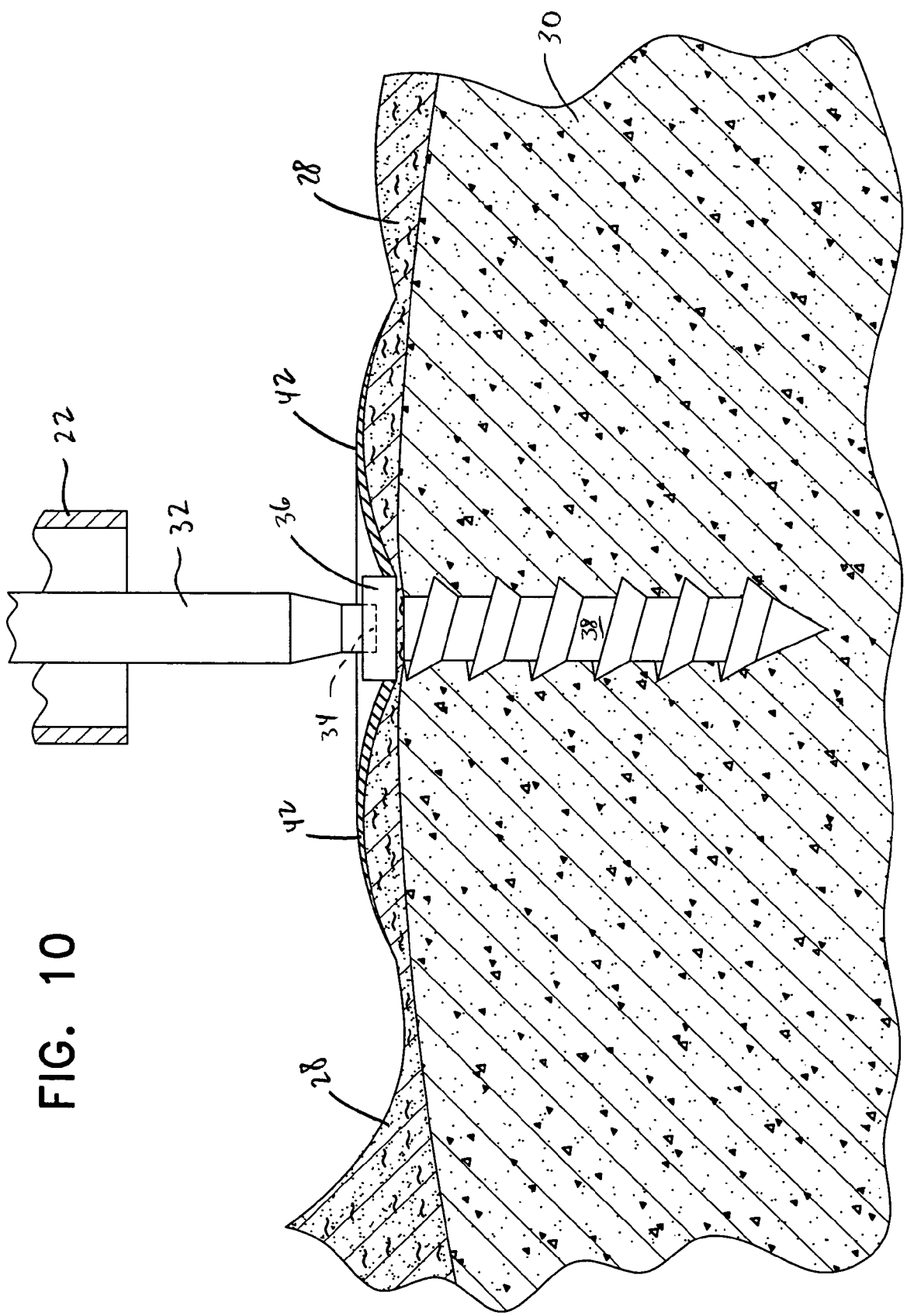
FIG. 10 is an enlarged view of FIG. 5 showing the tendon being compressed by the vanes of the fastener against the bone into which the screw has been driven.

The passage of the fastener through the cannula 22 is accomplished by folding the vanes to a retracted position extending substantially parallel to a longitudinal axis of the shaft portion 38 of the fastener 20. This is shown in FIGS. 6 and 7. Then as shown in FIG. 5, the fastener is further rotated and drawn from the cannula to an extended position of the vanes 42, as shown in FIGS. 8, 9 and 11. An enlargement of FIG. 5 is shown in FIG. 10.

As shown in a partial sectional view in FIG. 11, the head 36 and shaft portion 38 of the fastener 20 include a central longitudinal opening 46 for passage therethrough of a guide wire. The guide wire positions the fastener adjacent to the point of injury.

In addition, an O-ring 48 surrounds an uppermost portion of the shaft 38 adjacent to the head 36. The vanes 42 are pivotally connected to the O-ring 48. Therefore, as the vanes 42 contact the tendons, the shaft portion 38 is allowed to rotate relative to a fixed position of the O-ring 48 so as to maintain the relative positioning of the vanes with respect to the tendon 28 and bone 30.

Continued rotation of the fastener forces the tips 44 of the vanes to slide laterally across the tendon as the vanes 42 are moved down into further engagement with the tendon 28 as pushed by the head 36. The rotation of head 36 engages the portions of the vanes 42 mounted on the O-ring 48 so as to force the vanes laterally and downwardly, but without rotation of the vanes. The vanes as well as the entire fastener are coated with a biologically suitable coating to facilitate insertion of the shaft portion 38 as well as the sliding of the tips 44 of the vanes 42 across the tendon 28.

By this method, the vanes are moved into secure engagement with the tendons to entrap the tendons between the vanes and the bone. A plurality of orthopedic fasteners of the present invention may be used to secure the tendons to the bone. The fastener is made of plastic or metal compatible with the environment of bodily tissues.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. An orthopedic fastener for repair of torn rotator cuff tendons by securing the tendons to a bone, said orthopedic fastener comprising:
   a screw body having a shaft, said shaft having a tip and a head at opposite ends of the shaft,
   a circular O-ring surrounding the shaft and located adjacent to the head, said O-ring moving with the head, and
   a plurality of vanes, each vane having two ends, one end of said two ends of each of said plurality of vanes being pivotally mounted on said O-ring, the other of said two ends of each of said plurality of vanes being completely free to move freely away from a plane of a longitudinal axis of the screw body and said free end being located adjacent to the tip of the screw body in a retracted position, and said O-ring being movable through a cannula with the screw body for penetration of the screw body into bone,
   said plurality of vanes extending in said retracted position between said head and said tip and along the shaft of said screw body for passage through a cannula, said plurality of vanes being movable to an extended position extending substantially perpendicular to a longitudinal axis of the screw body for engaging and gripping of tendons to press the tendons against the bone while simultaneously the shaft is rotated into the bone as the screw body and the O-ring emerge from the cannula,
   each of said vanes being curved along an axis transverse to a longitudinal axis of each of the vanes.

2. The orthopedic fastener as claimed in claim 1, wherein the shaft includes spiral screw threads.

3. The orthopedic fastener as claimed in claim 2, wherein the screw body includes a longitudinally extending opening for passage of the screw body along a guide wire.

4. The orthopedic fastener as claimed in claim 1, wherein the head includes a slot for engagement by a screw driver.

5. The orthopedic fastener as claimed in claim 1, wherein there are four vanes.

6. The orthopedic fastener as claimed in claim 1, wherein said head of said screw body pushes said vanes from said retracted position into said extended position as said screw body is rotated into the bone.

7. A method of repairing torn rotator cuff tendons, said method comprising the steps of:
   making an incision in a shoulder region of a patient,
   passing a guide wire through the incision to a point of torn rotator cuff tendons,
   feeding a cannula and an orthopedic fastener along the guide wire to the point of the torn rotator cuff tendons, the orthopedic fastener including a screw body having a shaft, said shaft having a tip and a head at opposite ends of the shaft, an O-ring surrounding the shaft and located adjacent to the head, said O-ring moving with the head, and a plurality of vanes pivotally mounted on said O-ring and said O-ring being movable through the cannula with the screw body for penetration of the screw body into the bone, said plurality of vanes extending between said head and said tip and along the shaft of said screw body in a retracted position,
   passing a tool through the cannula to engage the head of the orthopedic fastener,
   rotating the orthopedic fastener and advancing the orthopedic fastener to pass through the tendons and to engage the bone,
   retracting the cannula during continued rotation of the orthopedic fastener, moving the plurality of vanes from in the retracted position through a cannula to an extended position extending substantially perpendicular to a longitudinal axis of the screw body for engaging and gripping of the tendons to press the tendons against the bone while simultaneously rotating the shaft into the bone as the screw body and the O-ring emerge from the cannula, and rotating the orthopedic fastener until the tendons are engaged and pressed against the bone by the plurality of vanes.

8. The method of repairing torn rotator cuff tendons as claimed in claim 7, wherein the orthopedic fastener includes a longitudinal opening through the screw body for passage along the guide wire.

9. The method of repairing torn rotator cuff tendons as claimed in claim 7, wherein said head of said screw body pushes said vanes from said retracted position into said extended position as said screw body is rotated into the bone.

10. The method of repairing torn rotator cuff tendons as claimed in claim 9, wherein there are four vanes.

11. An orthopedic fastener for repair of torn rotator cuff tendons by securing the tendons to a bone, said orthopedic fastener comprising:

a screw body having a shaft, said shaft having a tip and a head at opposite ends of the shaft, an O-ring surrounding the shaft and located adjacent to the head, said O-ring moving with the head, and a plurality of vanes pivotally mounted on said O-ring and said O-ring being movable through a cannula with the screw body for penetration of the screw body into bone, said plurality of vanes extending in a retracted position between said head and said tip and along the shaft of said screw body for passage through a cannula, said plurality of vanes being movable to an extended position extending substantially perpendicular to a longitudinal axis of the screw body for engaging and gripping of tendons to press the tendons against the bone while simultaneously the shaft is rotated into the bone as the screw body and the O-ring emerge from the cannula, the shaft including spiral screw threads, and the screw body including a longitudinally extending opening for passage of the screw body along a guide wire, each of said vanes being curved along an axis transverse to a longitudinal axis of each of the vanes.

* * * * *

UNITED STATES PATENT AND TRADEMARK OFFICE
CERTIFICATE OF CORRECTION

PATENT NO.      : 7,604,659 B2                                        Page 1 of 1
APPLICATION NO. : 10/983742
DATED           : October 20, 2009
INVENTOR(S)     : James M. Lee It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1380 days.

Signed and Sealed this

Fifth Day of October, 2010

David J. Kappos
*Director of the United States Patent and Trademark Office*